(12) United States Patent
Kamath et al.

(10) Patent No.: US 6,589,546 B2
(45) Date of Patent: *Jul. 8, 2003

(54) POLYMERIC COATINGS FOR CONTROLLED DELIVERY OF ACTIVE AGENTS

(75) Inventors: Kalpana R. Kamath, Natick, MA (US); James J. Barry, Marlborough, MA (US); Sepideh H. Nott, Melrose, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/006,889

(22) Filed: Dec. 10, 2001

(65) Prior Publication Data

US 2002/0054900 A1 May 9, 2002

Related U.S. Application Data (63) Continuation of application No. 09/204,259, filed on Dec. 3, 1998, now Pat. No. 6,335,029, which is a continuation-in-part of application No. 09/143,521, filed on Aug. 28, 1998, now abandoned.

(51) Int. Cl.[7] .......................... A61F 2/00; A61F 13/00; A61K 9/14
(52) U.S. Cl. ...................... 424/423; 424/422; 424/484; 424/486; 424/487; 424/488
(58) Field of Search ................. 424/422, 400, 424/423, 424, 425, 484, 486, 487, 488; 623/1, 11, 12

(56) References Cited

U.S. PATENT DOCUMENTS

| 5,091,205 A | | 2/1992 | Fan |
| 5,509,931 A | | 4/1996 | Schmitt |
| 5,527,353 A | | 6/1996 | Schmitt |
| 5,556,426 A | | 9/1996 | Popadiuk et al. |
| 5,609,629 A | * | 3/1997 | Fearnot et al. ............... 623/1 |
| 5,869,127 A | | 2/1999 | Zhong |
| 6,335,029 B1 | * | 1/2002 | Kamath ...................... 424/423 |

FOREIGN PATENT DOCUMENTS

| WO | WO 95/13313 | 5/1995 |
| WO | WO 96/12448 | 5/1996 |
| WO | WO 96/17634 | 6/1996 |
| WO | WO 97/38801 | 10/1997 |
| WO | WO 98/36784 | 8/1998 |
| WO | WO 99/00071 | 1/1999 |

* cited by examiner

Primary Examiner—Jose' G. Dees
Assistant Examiner—Sharmila S. Gollamudi
(74) Attorney, Agent, or Firm—Kenyon & Kenyon (57) ABSTRACT

Implantable medical device having a structure adapted for introduction into a patient wherein the structure is composed of a base material positioned over the structure. The implantable medical device further includes at least one composite layer of a bioactive agent and a polymer material and at least a barrier layer positioned over the composite layer and being of thickness adequate to provide a controlled release of the bioactive agent. The barrier layer being applied by a low energy plasma polymerization process which includes placing the device with the at least one composite layer in a plasma chamber and introducing at least one monomer gas.

23 Claims, 4 Drawing Sheets

POLYMERIC COATINGS FOR CONTROLLED DELIVERY OF ACTIVE AGENTS

This application is a continuation of 09/204,259, filed Dec. 3, 1998, now U.S. Pat. No. 6,335,029, which is a continuation-in-part of application Ser. No. 09/143,521, filed Aug. 28, 1998, now abandoned, both of which are incorporated herein in their entirety by reference thereto.

FIELD OF THE INVENTION

The present invention relates to methods and medical devices for the controlled, localized delivery of bioactive agents within a body.

BACKGROUND OF THE INVENTION

The systemic administration of drug agents, such as by intravenous means, treats the body as a whole even though the disease to be treated may be localized. Thus, it has become common to treat a variety of medical conditions by introducing an implantable medical device partly or completely into a body cavity such as the esophagus, trachea, colon, biliary tract, urinary tract, vascular system or other location within a human or veterinary patient. For example, many treatments of the vascular system entail the introduction of a device such as a stent, catheter, balloon, guide wire, cannula or the like. One of the potential drawbacks to conventional drug delivery techniques with the use of these devices being introduced into and manipulated through the vascular system, is that blood vessel walls can be disturbed or injured. Clot formation or thrombosis often results at the injured site, causing stenosis (closure) of the blood vessel.

Another cause of stenosis is vascular disease. Probably the most common disease causing stenosis of blood vessels is atherosclerosis. Atherosclerosis is a condition which commonly affects the coronary arteries, the aorta, the iliofemoral arteries and the carotid arteries.

Many medical devices and therapeutic methods are known for the treatment of atherosclerotic disease. One particular therapy for certain atherosclerotic lesions is percutaneous transluminal coronary angioplasty (PTCA). Another therapy for certain atherosclerotic lesions is percutaneous transluminal angioplasty (PTA). During PTA, a deflated balloon-tipped catheter is inserted in a patient's artery. The tip of the catheter is advanced to the site of atherosclerotic plaque. Inflation of the balloon "cracks" the atherosclerotic plaque and expands the vessel, thereby relieving the stenosis, at least in part.

While PTA presently enjoys wide use, it suffers from two major problems. First, the blood vessel may suffer acute occlusion immediately after or within the initial hour after the dilation procedure. Such occlusion is referred to as "abrupt closure." A second major problem encountered in PTA is the re-narrowing of an artery after an initially successful angioplasty. This re-narrowing is referred to as "restenosis" and typically occurs within the first six months after angioplasty. Restenosis is believed to arise through the proliferation and migration of cellular components from the arterial wall, as well as through geometric changes in the arterial wall referred to as "remodeling."

A device such as an intravascular stent including stent grafts and covered stents can be a useful adjunct to PTA, particularly in the case of either acute or threatened closure after angioplasty. The stent is placed in the dilated segment of the artery to mechanically prevent abrupt closure and restenosis. Unfortunately, even when the implantation of the stent is accompanied by aggressive and precise antiplatelet and anticoagulation therapy (typically by systemic administration), the incident of thrombotic vessel closure or other thrombotic complication remains significant, and the prevention of restenosis is not as successful as desired. Furthermore, an undesirable side effect of the systemic antiplatelet and anticoagulation therapy is an increased incidence of bleeding complications, most often at the percutaneous entry site.

Other conditions and diseases are also treatable with stents, catheters, cannulae and other devices inserted into the esophagus, trachea, colon, biliary tract, urinary tract and other locations in the body, or with orthopedic devices, implants, or replacements, for example. One of the drawbacks of conventional means of drug delivery using such devices is the difficulty in effectively delivering the bioactive agent over a short term (that is, the initial hours and days after insertion of the device) as well as over a long term (the weeks and months after insertion of the device). Another difficulty with the conventional use of stents for drug delivery purposes is providing precise control over the delivery rate of the desired bioactive agents, drug agents or other bioactive material. The term "bioactive agent" is used herein to mean any agent such as a pharmaceutical agent or drug or other material that has a therapeutic effect.

It is desirable to develop devices and methods for reliably delivering suitable amounts of therapeutic agents, drugs or bioactive materials directly into a body portion during or following a medical procedure, so as to treat or prevent such conditions and diseases, for example, to prevent abrupt closure and/or restenosis of a body portion such as a passage, lumen or blood vessel.

In view of the potential drawbacks to conventional drug delivery techniques, there exists a need for a device, method and method of manufacture which enable a controlled localized delivery of active agents, drug agents or bioactive material to target locations within a body.

SUMMARY OF THE INVENTION

The foregoing problems are solved and a technical advance is achieved in an illustrative vascular stent or other implantable medical device that provides a controlled release of at least one bioactive agent into the vascular or other system, or other location in the body, into which the stent or medical device is positioned. In one aspect, the present invention provides an implantable medical device having a structure adapted for introduction into a patient, e.g., a stent, coil, catheter, etc. The implantable medical device of the invention comprises at least one composite layer of a bioactive agent and a polymer material and at least one barrier layer positioned over the composite layer or layers. The barrier layer has a thickness adequate to provide a controlled release of the bioactive material. The barrier layer is applied to the medical device by a low energy plasma polymerization process which comprises placing the composite covered medical device in a plasma chamber and introducing at least one monomer gas into the chamber to form at least one barrier layer. In another embodiment of the invention, the barrier layer comprises at least one bioactive agent.

In another aspect, the present invention includes a method for the localized delivery of a bioactive agent to a target location within the body. The method includes the first steps of providing a medical device having a structure adapted for introduction into a patient wherein the structure is composed of a base material, at least one composite layer of a bioactive agent and a polymer material applied to the base material. At least one barrier layer is positioned over the composite layer and applied to the composite layer by a low energy plasma polymerization process. The barrier layer has a thickness adequate to provide a controlled release of the bioactive material. The plasma polymerization process includes the steps of placing the composite covered device in a plasma chamber and introducing at least one monomer gas into the plasma chamber to form at least one barrier layer on the outer surface of the composite covered device. The method for localized delivery of a bioactive material includes a second step of delivering the implantable medical device to the target location.

DETAILED DESCRIPTION

The present invention provides implantable medical devices and methods for the controlled, localized delivery of a bioactive agent to target locations within a body. The term "controlled localized delivery" as used herein is defined as a characteristic release rate of the bioactive agent over a desired period of time at a fixed location. The implantable medical devices of the present invention may have a simple construction, provide a minimal cross-sectional profile, and allow for easy and reproducible loading of active agents, drug agents and bioactive material.

Figure 1:
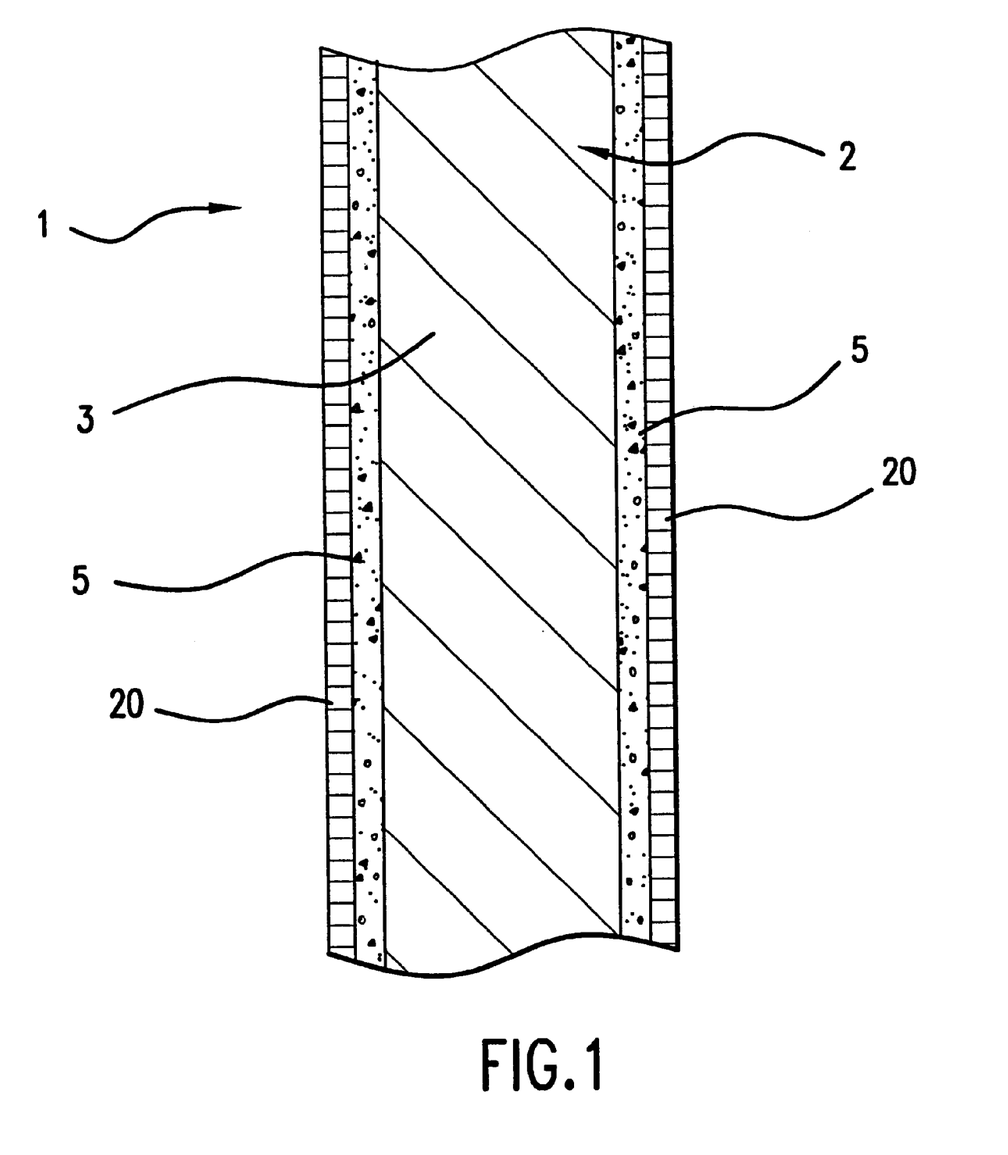
FIG. 1 is a cross-sectional view of a first preferred embodiment of the present invention.

With reference to FIG. 1, an implantable medical device 1 in accordance with the present invention is shown and includes a structure 2 adapted for introduction into a patient. The term "adapted" is used herein to mean that the structure 2 is shaped and sized for such introduction. For clarity, only a portion of structure 2 is shown in FIG. 1.

Figure 2A:
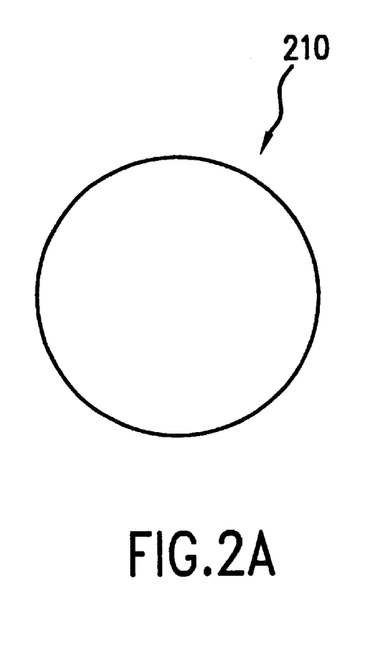
FIG. 2 shows side and end views of a stent used in an embodiment of the present invention.
Figure 2B:
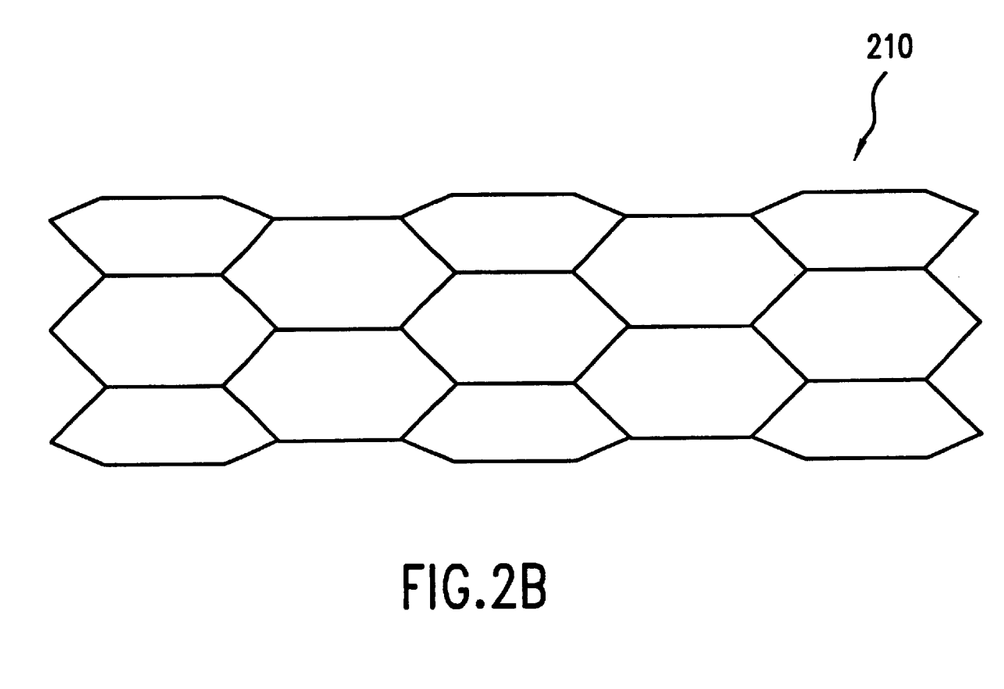

By way of example, structure 2 is configured as a stent particularly adapted for insertion into the vascular system of the patient. As known in the art, stents are tubular support structures that are implanted in coronary and peripheral blood vessels or arteries or other non-vascular lumens, blood vessels or other tubular body lumens. The present invention can thus be used for the dual purpose of localized drug delivery and stent placement, for example. The stent structure may also be used in non-vascular systems and sites such as the esophagus, trachea, colon, biliary ducts, urethra, and ureters, among others. A stent 210 used with the present invention is of any suitable design and is configured in mesh design as shown in FIG. 2.

Referring back to FIG. 1, structure 2 is alternatively configured as any conventional vascular or other medical device, and includes any of a variety of conventional stent or other adjuncts, such as helically wound strands, perforated cylinders or the like. Accordingly, the structure 2 is configured as at least one, or any portion of, a medical device that is adapted for insertion into the body. Examples of such medical devices include catheters, guide wires, balloons, filters (e.g., vena cava filters), stents, stent grafts, vascular grafts, intraluminal paving systems, implants and other devices used in connection with drug-loaded polymer coatings. Such devices are implanted or otherwise utilized in body lumens and organs such as the coronary vasculature, esophagus, trachea, colon, biliary tract, urinary tract, prostate, brain, and the like. Examples of suitable vascular grafts are described in U.S. Pat. Nos. 5,509,931, 5,527,353, and 5,556,426. Vena cava filters such as those described in WO 96/12448 and WO 96/17634 may also be used in the present invention. All of foregoing documents identified by number are incorporated herein in their entireties.

The grafts, including stent grafts, that are provided with a bioactive agent-polymer composite layer in accordance with the present invention include synthetic vascular grafts that are used for replacement of blood vessels in part or in whole. A typical vascular graft is a synthetic tube with each end thereof sutured to the remaining ends of a blood vessel from which a diseased or otherwise damaged portion has been removed. In a typical stent graft, each end of the synthetic tube portion includes a stent that is affixed to each of the remaining ends of a blood vessel from which a diseased or otherwise damaged portion has been removed. Alternatively in a stent graft, the replacement vessel may be a segment of a vessel removed from another location in the patient, such as a portion of a femoral artery or the like. In the case of a synthetic graft, the graft is typically tubular and may be, e.g., of a woven, knit or velour construction. Preferred base materials for the grafts and covering material for the stent grafts include polyethylene terephthalate and polytetrafluoroethylene. The vascular grafts may be reinforced with, for example, helices, rings, etc. in order to provide uniform strength over the entire surface of the graft tubing. The materials with which such grafts are constructed are biologically compatible materials including, but not limited to, thermoplastic materials such as polyester, polytetrafluoroethylene (PTFE), silicone and polyurethanes. The preferred materials include polyester fibers and PTFE.

Examples of other suitable grafts are described in U.S. Pat. Nos. 5,509,931, 5,527,353, and 5,556,426, all of which are herein incorporated by reference. In a most preferred embodiment of the invention, the graft is provided with a composite layer of polymeric material/paclitaxel, and most preferably, the polymeric material is a polyurethane and derivatives thereof. This polymer/paclitaxel composite-coated graft, when positioned at a desired site in the body provides an extended release of paclitaxel to the site.

Turning back to FIG. 1, structure 2 is composed of a base material 3 which is compatible with the intended use of structure 2. The base material 3 is preferably biocompatible.

A variety of conventional materials may be employed as the base material 3. For example, the base material 3 may be either elastic or inelastic. The base material 3 may be either biodegradable or nonbiodegradable. Moreover, some biologic agents have sufficient strength to serve as the base material 3 of structure 2, even if not especially useful in the exemplary coronary stent.

Accordingly, the base material 3 may be formed of stainless steel, tantalum, titanium, nitinol, gold, platinum, inconel, iridium, silver, tungsten, or another biocompatible metal, or alloys of any of these; carbon or carbon fiber; cellulose acetate, cellulose nitrate; silicone, polyethylene terephthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these. Stainless steel and nitinol are particularly useful as base materials when the structure 2 is configured as a vascular stent.

The implantable medical device 1 of the present invention also includes at least one layer 5 formed by a composite of at least one bioactive agent and a biocompatible polymeric or copolymeric material. When multiple polymer-bioactive agent composite layers are used, the layers may contain the same or different bioactive agents and/or the same or different polymers. The combination of bioactive agent and polymer serves as a monolithic matrix depot of the bioactive agent. This depot contributes partially to providing control over the release rate of the bioactive agent from the medical device.

The composite layer(s) are formed from a solution or dispersion (e.g. suspension, emulsion, or semisolid) which is applied to at least a portion of the surface of the base material 3 to form the polymer-bioactive agent composite layer 5. The terms "bioactive agent", "drug agent" and "bioactive material" are used interchangeably herein. The application of polymer-bioactive agent composite 5 onto at least a portion of the base material 3 may be accomplished by a physical method such as, but not limited to, spraying, dipping, painting, electrostatic interaction, physical adsorption or covalent method such as, but not limited to, chemical attachment to the base material 3. The polymer-bioactive agent composite layer 5 is preferably capable of incorporating a substantial amount of bioactive agent, such as, for example, 0.2 $\mu g/mm^2$ to 20 $\mu g/mm^2$. The percent of drug in composite layer 5 can be varied from 1% to 50% w/w. The polymer-bioactive agent composite layer 5 is typically applied at a thickness of greater than 1 micron, preferably a thickness of about 5–50 microns and most preferably a thickness of about 5 to 25 microns in order to adjust the bioactive agent dosage. Very thin polymer-bioactive agent composites, e.g., of about 0.2–0.3 microns are also possible optionally, multiple layers of polymer-bioactive agent composites may be applied onto the outer surface of the base material (or part(s) thereof) 3 of structure 2. Such multiple layers can be of the same or different polymer materials and/or bioactive agents.

A vast range of bioactive agents may be incorporated in composite layer 5 as long as the selected bioactive material survives the processes required for application of the bioactive agent-polymerization composite layer onto the device, e.g., plasma polymerization or vapor deposition. Particularly useful in the practice of the present invention are bioactive agents which prevent or ameliorate abrupt closure and restenosis of blood vessels previously opened by stenting surgery or other procedures.

The bioactive agents used in the present invention are selected from a number of therapeutic agents depending on the desired application. For example, these therapeutic agents include anti-inflammatory agents such as dexamethasone, prednisolone, corticosterone, budesonide, estrogen, sulfasalazine, mesalamine, and analogues thereof; antineoplastic/antiproliferative/antimiotic agents such as paclitaxel, 5-fluorouracil, cisplatin, vinblastine, vincristine, epothilones, endostatin, angiostatin, tyrosine kinase inhibitors, and analogues thereof; anesthetic agents such as lidocaine, bupivacaine, ropivacaine, and analogues thereof; anti-coagulants; angiogenic factors and growth factors; and genes encoding for such growth factors and other inhibitory or stimulatory proteins/factors. Also included are nucleic acid compounds such as antisense oligonucleotides, ribozymes, and genes carried by viral vectors (retro, adeno, adenoassociated, lenti, ebola, herpes simplex, etc.) and non viral systems (plasmid, cationic lipid materials, compacting agents, etc.)

The bioactive agents useful in accordance with the present invention may be used singly or in combination. For example, an anti-proliferative agent such as paclitaxel may be used in combination with another drug agent, such as an anticoagulant, anti-inflammatory, antithrombogenic, thrombolytic, nitric oxide-containing polymer, or a vascular cell promoter such as VEGF and FGF, for example.

Paclitaxel is a preferred drug agent for use with the present invention either alone or in combination with another drug agent, as described above. Paclitaxel is a complex alkaloid extracted from the Pacific Yew Taxus brevifolia Family (Family Taxacea) which has been demonstrated to have antiproliferative activity. As used herein, paclitaxel includes the alkaloid and any pharmacologically active derivative or analog thereof. Thus paclitaxel includes naturally occurring forms and derivatives thereof and synthetic and semi-synthetic forms thereof. TAXOL® (Bristol-Meyers Squibb Company) is a commercially available form of paclitaxel. These and other compounds are added to the polymer material using similar methods and routinely tested as set forth in the specification. Any modifications are routinely made by one skilled in the art.

The biocompatible polymeric material used to form the bioactive agent-polymer composite layer(s)may include any polymeric material capable of forming a solidified composite layer in the presence of the bioactive material. The polymeric material of the present invention is hydrophilic or hydrophobic, and is, for example, polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, polyolefins, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. Composite layer 5 can include of a single polymer or copolymer. It may also include copolymers or physical blends of any of the materials indicated above. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In a most preferred embodiment of the invention, the polymer is a polyurethane and derivatives thereof.

The use of the bioactive agent-polymer composite layer 5 in the present invention has the added advantage in that this layer or multilayers allow for enhanced adhesion of the mixture to the base material 3 as opposed to the prior art methods of first applying a polymer followed by a drug coating. The bioactive agent-polymer composite layer 5 also provides for an effective way of adjusting the amount of the bioactive agent placed on the base material 3. This is accomplished by adjusting the bioactive agent/polymer ratio and/or thickness of the bioactive agent-polymer composite layer. Also, composite layer 5 provides a co-compliant surface for a subsequent barrier layer and aids in maintaining the mechanical integrity of the barrier layer during the expansion of the medical device. The bioactive agent-polymer composite also has the added benefit of providing a blood compatible surface to the medical device. Thus, the biocompatible polymer material acts as an intermediary between the vascular walls or the blood stream and the implantable medical device 1.

The release profile of the drug from the bioactive agent-polymer composite layer 5 is determined by many factors including the drug solubility, the amount of the drug applied, the drug-to-polymer ratio in composite layer 5 and the thickness and porosity of the composite layer. The release profile is also regulated by the presence of an outer barrier layer which is formed by a vapor deposition process or a low energy plasma polymerization process.

Still with reference to FIG. 1, implantable medical device 1 of the present invention also includes at least one barrier layer 20 positioned over the bioactive agent-polymer composite layer(s) 5. One purpose of this barrier layer or layers is to provide further controlled release of the bioactive material when device 1 is positioned in the vascular system or other body lumen of a patient. The thickness of the barrier layer 6 is chosen so as to provide such control. Also, the barrier layer 20 protects the drug from the routine handling process and physiologic milieu until the drug reaches the target site. In an alternative embodiment of the invention, the barrier layer(s) may contain an additional bioactive agent which may be the same or different from the bioactive agent of the bioactive agent-polymer composite layer(s).

The barrier layer 20 is a polymer or copolymer layer deposited on the outer surface of the bioactive agent-polymer composite layer 5 by a vapor deposition process or a low energy plasma polymerization process. Low-energy plasma polymerization is performed by exposing the composite coated implantable medical device to a monomer gas at the inception of the plasma polymerization process. The bioactive agent-polymer composite-coated device is placed in a plasma chamber or other similar device and exposed to a monomer gas such as, for example, silicone-based monomers such as cyclic or acyclic siloxanes, silanes, silylimidazoles; fluorine-based monomers such as hydrofluorocarbons; aliphatic or aromatic hydrocarbons; acrylic monomers; N-vinyl pyrrolidone; ethylene oxide or combinations thereof. The monomer gas may have functional groups to allow covalent attachment of appropriate drugs by anchoring to these functional groups. Polymer blends, copolymers, or interpenetrating networks can be deposited in addition to homopolymer deposition, by simultaneous or subsequent introduction of two or more monomer gases. When introduced as a mixture, the ratio of the monomer gases could be adjusted to obtain desired properties. An energy source such as a radio frequency energy source is used to produce the low energy generating process.

Alternatively, the barrier layer can be applied by the vapor deposition process. Examples of polymers that can be deposited in such a manner are parylene or polyamides. For deposition of parylene using this process, the monomer vapor of p-xylylene formed by high temperature pyrolysis of its dimer form, is condensed at temperatures of 50 C. or lower on the surface of composite layer (5) to form the barrier layer polymer.

Low-energy plasma generates active species in a circulating monomer gas, a polymer is formed and is subsequently deposited on the outer surface of the previously-coated device. The plasma may also generate active species on the device to be coated along with the monomer gas. This leads to plasma grafting in addition to plasma polymerization. Properties of the low-energy plasma polymerization barrier layer (i.e., the thickness and/or cross-linking density of the formed polymer) are controlled, for example, by the monomer flow rate, pressure and power of the plasma supplied, reaction time, and combinations thereof in a manner such that the properties of the bioactive agent(s) are not negatively effected.

The use of low-energy plasma polymerization provides for elimination of thermal effects of typical polymerization methods because the low-energy process occurs at room temperature. Also, since the monomer is introduced in a gaseous form, in the plasma chamber, no solvents are necessary for the application to the bioactive agent-composite layer. Furthermore, since the time frame used for the low-energy process is small, the possibility of any adverse effects to the bioactive agent is minimal.

Another purpose of barrier layer 20 is to provide protection of the bioactive agent-polymer composite layer 5 from damage that may occur, e.g., from handling of the device, such as during maneuvering of the device through the body until it is placed at the desired target site. This could be achieved in one or more different way.

For example, the plasma polymerization process allows covalent anchoring of the barrier layer 20 to the polymer matrix in the composite layer 5. The formation of covalent bonds between the composite layer 5 and the barrier layer 20 subsequently offers a stronger adhesion of the barrier layer 20 and hence an enhanced protection of the drug depot in the composite layer 5 in comparison to that offered by other methods described in the prior art.

Also, in the case of a hydrophobic barrier layer, the diffusion of water from the physiologic environment is restricted, thus limiting contact of the bioactive agent with the eluting environment.

Additionally, the barrier layer formed by plasma polymerization is cross-linked in nature as opposed to barrier layers formed by other approaches described in the prior art. The degree of cross-linking can be varied by varying the plasma polymerization process parameters, such as the power. An added endurance could be obtained by increasing the cross-linking density and hence a more rigid barrier layer, while lowering the cross-linking density provides a more flexible barrier layer.

The at least one barrier layer 20 of the present invention is preferably less than 5000Å thick and optimally about 50–2000Å thick.

As noted above, the release profile of the bioactive material from the medical device is determined by many factors including the solubility of the bioactive agent in the barrier layer, porosity of both the composite and barrier layers, cross-linking density and thickness of the barrier layer, and hence resistance to the transport of the bioactive agent through the barrier layer.

Figure 3:
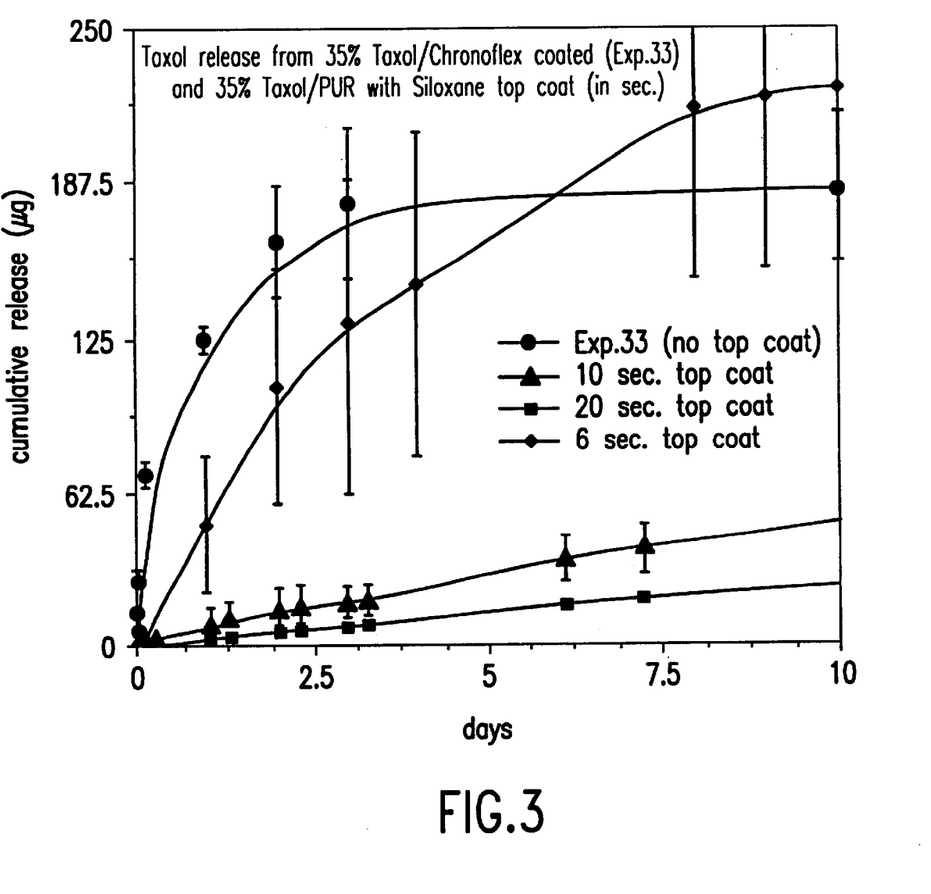
FIG. 3 shows a release profile of the effect of increasing the plasma polymerization time for a siloxane barrier layer in which paclitaxel is released.

FIG. 3 shows the effects of increasing the plasma polymerization time on the release rate of the bioactive agent. In FIG. 3, a siloxane barrier layer is applied onto a paclitaxel-polyurethane composite layer of a stent by a low energy plasma polymerization process including polyurethane and derivatives thereof including polycarbonate based, polyurea based, polyether based, and polyester based derivatives. Also included are Inter-Penetrating Network (INP)s such as siliconized polyurethane. The paclitaxel-polyurethane-coated stent is exposed to gaseous monomers of tetramethylcyclotetrasiloxane, which are then polymerized by low energy plasma polymerization onto the surface of the paclitaxel-polyurethane coating. As can be seen from FIG. 3, it is possible to achieve progressively slower release profiles of paclitaxel by increasing the plasma polymerization times, for example, from 6 seconds to 10 seconds to 20 seconds. An increase in polymerization time results in the formation of a thicker siloxane barrier layer, which in turn causes a sustaining effect on the paclitaxel release rate. Thus, the release profile of paclitaxel or other bioactive agent is precisely controlled by varying the time of the low energy plasma polymerization process.

Furthermore, modifications of any one or more of the basic plasma parameters such as the plasma polymerization time, the monomer flow rate, the pressure, and the energy applied offers the possibility of either changing the thickness and/or cross-linking density of the formed polymer. Both of these properties can, in turn, provide a means to control drug release by offering an enhanced resistance to the drug elution from the composite layer. Also, since the low energy plasma polymerization process utilizes gaseous phase for polymer application, coating selective areas on the coated stent may easily be achieved (by masking appropriate areas), which is difficult to achieve in a solution phase coating application.

Figure 4:
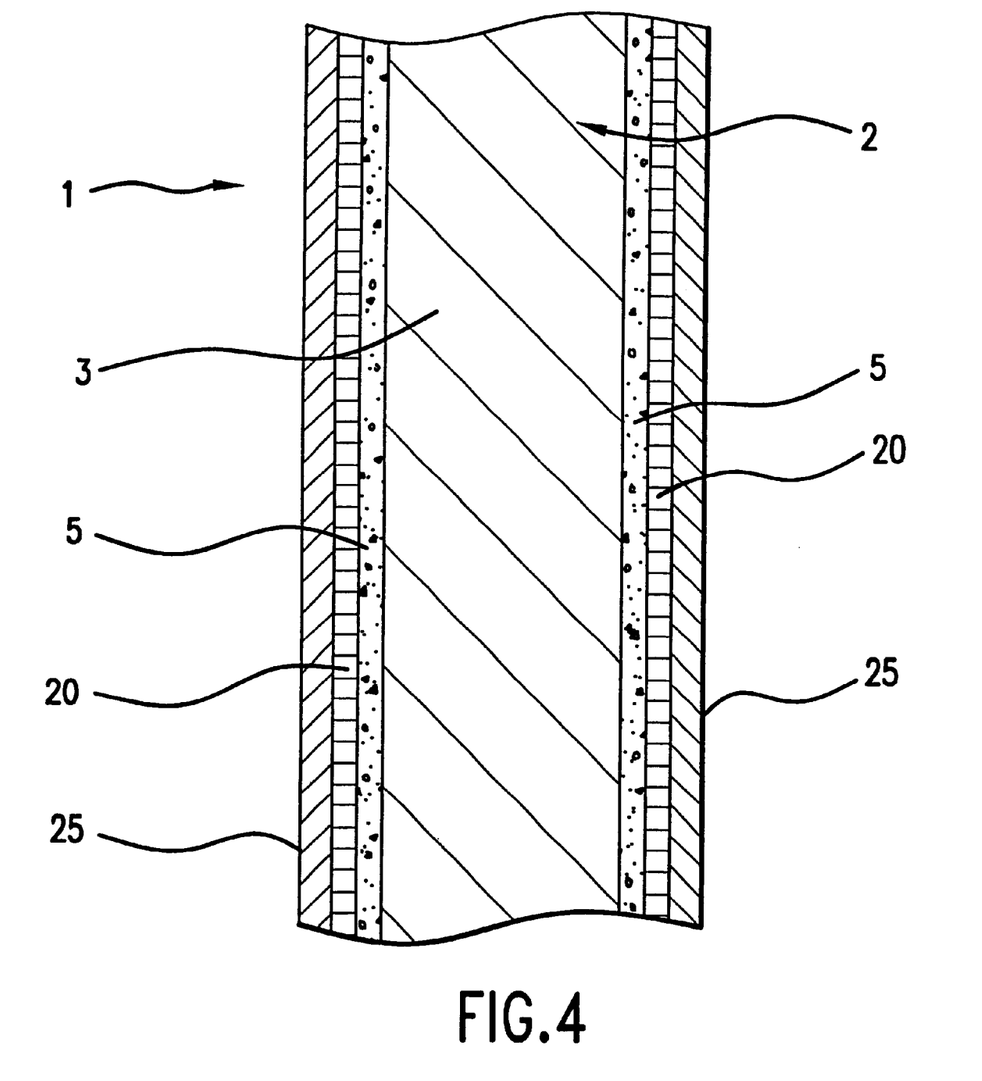
FIG. 4 is a cross-sectional view of a preferred embodiment of the present invention.

In an alternative embodiment, a bioactive material(s) is incorporated into or on the outer surface of the barrier layer. For example, a second bioactive material is introduced into the barrier layer 20 by any suitable method. FIG. 4 shows a stent having an outer coating of bioactive agent, such as heparin, which is applied to barrier layer 20 to produce layer 25. The outer bioactive material, which may be the same or different from the bioactive agent of the bioactive agent-polymer composite layer, is placed in solution and applied to the barrier layer 20 by any suitable means, including dipping the coated medical device into the drug solution or by applying the solution onto the layer 20 such as by spraying. In the former method, the amount of bioactive material loading is controlled by regulating the time the barrier layer is exposed to the drug solution or dispersion, the extent of polymer cross-linking, the concentration of the drug in the solution or dispersion and/or the amount of barrier layer applied to the medical device.

The barrier layer with the second bioactive drug may have a similar composition or may differ physically or chemically from the first barrier layer. The nature of the second barrier layer would be dictated by the physicochemical properties of the second drug to be incorporated on the outer surface. For example, for the incorporation of hydrophilic agent, such as heparin, the second barrier layer may include a hydrophilic/hydrophobic polymer network formed by plasma polymerization. The hydrophilic component may be provided by plasma polymerization of monomers such as, N-vinyl pyrrolidone or ethylene oxide, while the hydrophobic component is provided by siloxane-based polymers. The incorporation and release of the hydrophilic bioactive agent is thus facilitated due to its higher affinity for the hydrophilic polymer. In such a situation, the drug release occurs by dissolution/erosion of the hydrophilic polymeric component followed by diffusion through the hydrophobic counterpart.

In the event that the bioactive material used in the layer 5 is the same as the bioactive material in layer 20, the bioactive material of layer 5 provides an initial bolus loading dose required to reach the therapeutic window, which is further maintained by the bioactive agent-polymer composite layer 5.

In the event that the bioactive material of layer 5 is different from the bioactive material used with layer 20, the bioactive material in layer 20 provides a combination of biological effects achieved by either a synergistic or independent bioactivity of the two bioactive materials. For example, a combination of paclitaxel with corticosteroids or nitric oxide or nitric oxide donors as the bioactive material provides a synergistic effect. An example of a combination of bioactive agents that provide independent bioactivity useful for the treatment of restenosis is paclitaxel and heparin. In another example, heparin, heparin binding growth factors and nitric oxide donor are incorporated within the barrier layer 20 to obtain multiple benefits of non-thrombogenecity and enhanced endothelialization. In an additional embodiment, layer 20 includes proteins or biological moieties to further modulate the drug release from layer 20.

When implanted, a substantial amount of the bioactive material contained in the bioactive agent-polymer composite layer 5 of the medical device is diffused into the affected area over an extended period of time and in a controlled manner.

The present invention provides a device, method of treatment and method of manufacture which controls the localized delivery of active agents, drug agents or bioactive material to target locations within a body. Although the present invention has been described with respect to several exemplary embodiments, there are many other variations of the above-described embodiments which will be apparent to those skilled in the art, even when elements have not explicitly been designated as exemplary. It is understood that these modifications are within the teaching of the present invention, which is to be limited only to the claims appended hereto.

What is claimed is:

1. An implantable medical device comprising:
   a structure adapted for introduction into a patient, wherein the structure comprises a base material;
   at least one layer comprised of at least one bioactive agent in a polymer matrix, applied to at least a portion of the outer surface of said base material; and
   at least one barrier layer positioned over the layer comprised of at least one bioactive agent in a polymer matrix, said barrier layer having a thickness adequate to provide controlled release of the at least one bioactive agent;
   wherein said barrier layer is formed in situ by a low energy plasma polymerization process.

2. The device of claim 1, further comprising a drug layer over said barrier layer wherein said drug layer includes heparin.

3. A method for the localized delivery of a drug agent to a target location within a body, comprising the steps of:
   A) providing an implantable medical device which comprises a coated structure adapted for introduction into a patient, the structure comprising:

(a) a base material;
(b) at least one layer comprised of at least one bioactive agent in a polymer matrix, applied to at least a portion of the outer surface of said base material;

B) forming at least one barrier layer comprising a polymer over the layer comprised of at least one bioactive agent in a polymer matrix, wherein said at least one barrier layer has a thickness adequate to provide a controlled release of the at least one bioactive agent, wherein said barrier layer is applied by a low energy plasma polymerization process which comprises:
(i) placing said coated structure in a chamber;
(ii) introducing at least one monomer gas into said chamber; and
(iii) exposing the gas to a low energy source, whereby the monomer gas forms a barrier layer on the outer surface of the medical device;

C) introducing additional bioactive agent into said at least one barrier layer; and D) delivering said implantable medical device to said target location.

4. The device of claim 1, wherein the barrier layer comprises a bioactive ingredient.

5. The device of claim 1, wherein said barrier layer is applied by a low energy plasma polymerization process which comprises:
(i) placing said coated structure in a chamber;
(ii) introducing at least one monomer gas into said chamber; and
(iii) exposing the gas to a low energy source, whereby the monomer gas forms a barrier layer on the outer surface of the medical device.

6. The device of claim 1, wherein the base material comprises stainless steel or nitinol.

7. The device of claim 1, wherein the bioactive agent in the barrier layer ranges from 0.2 $\mu g/mm^2$ to 20 $\mu/mm^2$.

8. The device of claim 1, wherein the bioactive agent in the barrier layer ranges from 1% to 50% w/w of the polymer matrix.

9. The device of claim 1, wherein the polymer matrix has a thickness in the range of about 5 to about 25 microns.

10. The device of claim 1, wherein the bioactive agent comprises paclitaxel and nitric oxide.

11. A method of making an implantable medical device comprising:
A) providing an implantable medical device which comprises a coated structure adapted for introduction into a patient, the structure comprising:
(a) a base material;
(b) at least one layer comprised of at least one bioactive agent in a polymer matrix, applied to at least a portion of the outer surface of said base material;
B) forming at least one barrier layer comprising a polymer over the layer comprised of at least one bioactive agent in a polymer matrix, wherein said at least one barrier layer has a thickness adequate to provide a controlled release of the at least one bioactive agent.

12. The method of claim 11, wherein said barrier layer is applied by a low energy plasma polymerization process which comprises:
(i) placing said coated structure in a chamber;
(ii) introducing at least one monomer gas into said chamber; and
(iii) exposing the gas to a low energy source, whereby the monomer gas forms a barrier layer on the outer surface of the medical device.

13. The device of claim 12, wherein said monomer gas is selected from the group consisting of a cyclic or acyclic siloxane silicon-based monomers, silane silicon-based monomers, silylimidazoles silicon-based monomers, hydrofluorocarbon-based monomers; aliphatic or aromatic hydrocarbon-based monomer; acrylic monomer; and combinations thereof.

14. The implantable device of claim 11, wherein said polymer material comprises a polymer selected from the group consisting of polyurethane, polycarboxylic acids, polyorthoesters, polyvinylpyrrolidone, maleic anhydride polymers, polyamides, polyvinyl alcohols, polyethylene oxides, glycosaminoglycans, proteins, polypeptides, silicones, polysaccharides, polyesters, polyacrylamides, polyethers, copolymers of vinyl monomers, and mixtures and copolymers thereof.

15. The device of claim 11, wherein said at least one bioactive agent is paclitaxel.

16. The device of claim 11, wherein said at least one composite layer is formed by dissolution, dispersion, absorption, or adsorption of said at least one bioactive agent and polymer material.

17. The device of claim 11, wherein the thickness of said at least one barrier layer is less than 5000 Å.

18. The device of claim 17, wherein the thickness of said at least one barrier layer is about 50 to 2000 Å.

19. The device of claim 11, wherein the medical device is a device selected from the group consisting of a catheter, wire guide, cannula, stent graft, covered stent, vascular or other graft, cardiac pacemaker lead or lead tip; an angioplasty device or portion thereof; and any portion thereof.

20. The device of claim 11, wherein the base material of the structure comprises at least one of metal or polymer.

21. The device of claim 11, further comprising a drug layer over said barrier layer.

22. The device of claim 11, wherein said drug layer includes heparin.

23. An implantable medical device comprising:
a structure adapted for introduction into a patient, wherein the structure comprises a base material;
at least one layer comprised of at least one bioactive agent in a polymer matrix, applied to at least a portion of the outer surface of said base material; and
at least one barrier layer positioned over the layer comprised of at least one bioactive agent in a polymer matrix, said barrier layer having a thickness adequate to provide controlled release of the at least one bioactive agent;
wherein said barrier layer is formed in situ by a low energy plasma polymerization process of a monomer gas;
wherein the at least one bioactive agent is paclitaxel;
wherein the thickness of said at least one barrier layer is about 50 to 2000 Å;
wherein the bioactive agent in the barrier layer ranges from 0.2 $\mu g/mm^2$ to 20 $\mu g/mm^2$.

* * * * *